(12) United States Patent
Aoyagi

(10) Patent No.: US 6,363,734 B1
(45) Date of Patent: Apr. 2, 2002

(54) AIR CONDITIONING SYSTEM EQUIPPED WITH STERILIZATION/DEODORIZATION GAS SUPPLY MEANS

(75) Inventor: Kohei Aoyagi, Tokyo (JP)

(73) Assignee: Kabushiki Kaisha Sunseal, Osaka-fu (JP)

( * ) Notice: Subject to any disclaimer, the term of this patent is extended or adjusted under 35 U.S.C. 154(b) by 0 days.

(21) Appl. No.: 09/691,080

(22) Filed: Oct. 18, 2000

(30) Foreign Application Priority Data

May 2, 2000 (JP) .................................... 2000-133716

(51) Int. Cl.[7] .............................. F25D 23/00; A62B 7/08
(52) U.S. Cl. ............................. 62/264; 62/78; 422/124
(58) Field of Search ........................... 62/78, 303, 317, 62/264; 422/24, 123, 124, 125, 120

(56) References Cited

U.S. PATENT DOCUMENTS

| | | | |
|---|---|---|---|
| 3,990,848 A | * 11/1976 | Corris | |
| 4,601,886 A | * 7/1986 | Hudgins | 422/124 X |
| 5,015,442 A | * 5/1991 | Hirai | 422/124 X |
| 5,919,422 A | * 7/1999 | Yamanaka et al. | 422/121 |
| 5,989,497 A | * 11/1999 | Labonte, Jr. | 422/123 X |
| 6,264,548 B1 | * 7/2001 | Payne, Jr. et al. | 422/123 X |

FOREIGN PATENT DOCUMENTS

| | | | |
|---|---|---|---|
| JP | 63108137 A | * | 5/1988 |
| JP | 63108138 A | * | 5/1988 |
| JP | 08312977 A | * | 11/1996 |
| JP | 10253096 A | * | 9/1998 |

* cited by examiner

Primary Examiner—Denise L. Esquivel
Assistant Examiner—Chen-Wen Jiang
(74) Attorney, Agent, or Firm—Dennis G. LaPointe; Mason & Associates, PA

(57) ABSTRACT

Disclosed is an air conditioning system that comprises a sterilization/deodorization gas supply device wherein a sterilization/deodorization gas supply unit, which includes a chemical container and an evaporation acceleration unit, for accelerating the evaporation of a chemical stored in a container, is located along an air channel extending from an air inlet to a heat exchanger. An appropriate amount of a sterilization/deodorization gas is mixed with cooled or heated air that is discharged from the air conditioning system, so that the generation of bad odors, which are generated by mold and microorganisms, and the growth and dispersion of bacteria can be suppressed.

9 Claims, 2 Drawing Sheets

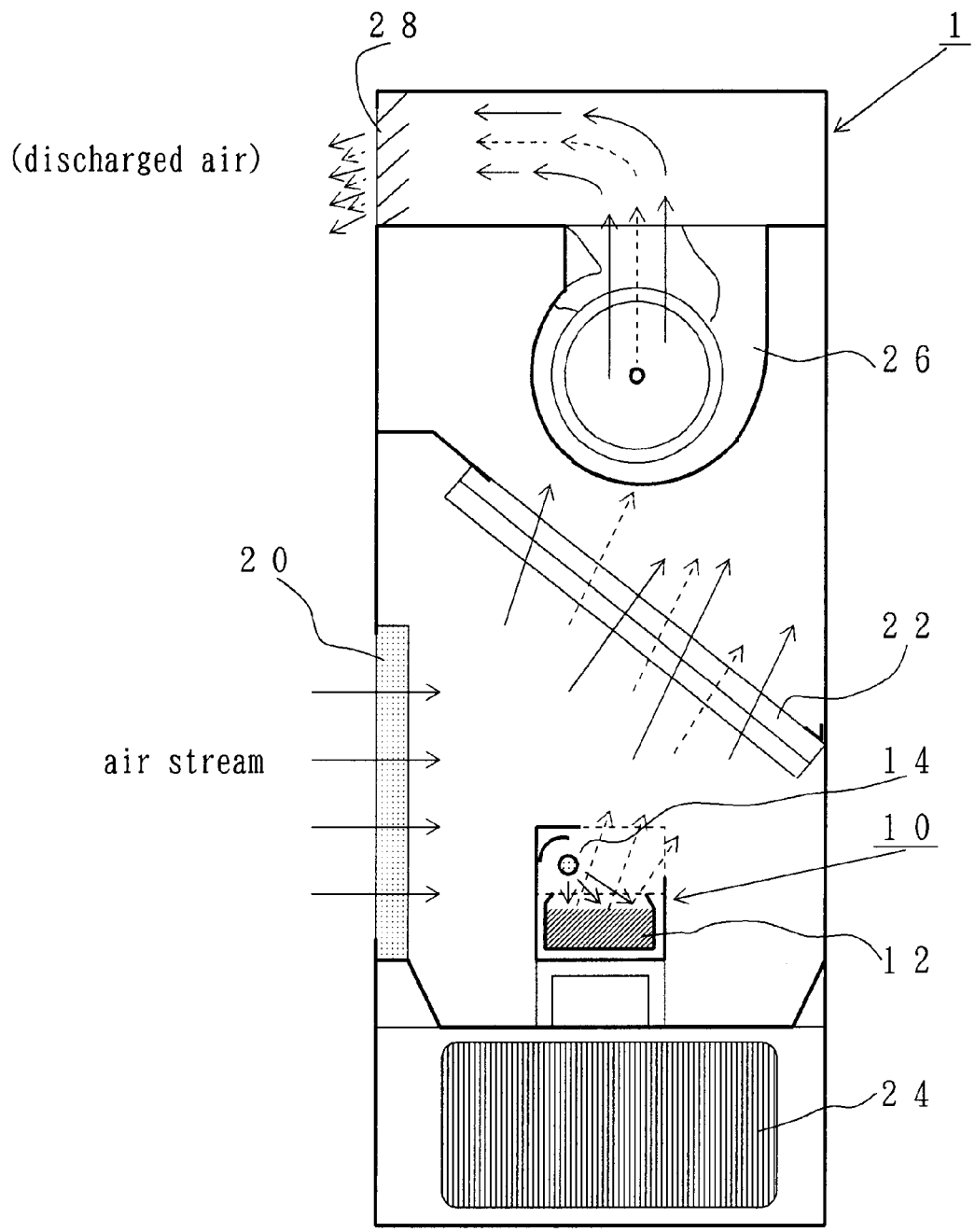
F I G. 1

AIR CONDITIONING SYSTEM EQUIPPED WITH STERILIZATION/DEODORIZATION GAS SUPPLY MEANS

BACKGROUND OF THE INVENTION

1. Field of the Invention

The present invention relates to an air conditioning system including means for the supply of a sterilization/deodorization gas, and relates in particular to an air conditioning system comprising means for using a liquid or gel form of a chemical to easily and stably supply a sterilization/deodorization gas.

2. Related Arts

There can be no disagreement with the statement that in today's society air conditioning systems, such as mechanical devices for cooling or heating, or air purifiers, for cleaning air, constitute indispensable items of equipment. Various types of air conditioning systems, which are intended for use in small spaces, such as ordinary residences and small stores, and for use in larger spaces, such as large offices, factories, clean rooms, department stores, supermarkets, sleeping accommodations such as hotels and inns, hygienic and medical accommodations, homes for the aged, hospitals, playhouses and movies, public halls and entertainment halls, and indoor stadiums.

These air conditioning systems are so designed that thermal exchanges are effected by blowing cooled or heated air, produced by various types of refrigerating or heating sources, through air passages of various lengths into enclosed spaces. But when such an air conditioning system is used for an extended period of time, dust and dirt tend to accumulate inside the system, especially in the heat exchange section and on the walls of the air passages, and as has often been pointed out, these accumulations of dust and dirt act as hotbeds for the growth of microorganisms and mold, which are responsible for the production of unwanted odors, and infectious bacteria and irritants, such as those that are associated with respiratory infections, allergies and asthma.

To eliminate such a problem, mesh filters are provided at air intakes to prevent the entry of dirt and dust, or filters containing an absorption material, such as active carbon, active clay or silica gel, are provided at air outlets. However, since the deterioration of all such filters proceeds progressively, the resistance to the passage of air through the filters increases apace, and energy consumption rises accordingly. And if the filters are not properly cleaned and maintained, excessive dust and dirt will collect on them and their continued employment will produce adverse effects.

Therefore, consideration has been given to the employment inside air conditioning systems of materials, or an antibacterial material, to which dust and dirt are not easily attached, but it is difficult to obtain materials that will stably demonstrate the desired effects over an extended period of time. Thus, a demand has arisen for means to easily and stably perform the sterilization and deodorization of air conditioning systems.

To stably perform sterilization and deodorization, the present inventor found that when appropriate vaporization acceleration means is used, together with a stabilized chlorine dioxide liquid or gel that is safe to handle, a stabilized chlorine dioxide gas obtained as a transpiration gas was effective.

SUMMARY OF THE INVENTION

To resolve the above shortcoming, it is one objective of the present invention to provide an air conditioning system comprising means for supplying a sterilization/deodorization gas which, when mixed in an appropriate quantity with cooled or heated air in the air conditioning system, suppresses the generation of bad odors, produced by microorganisms and mold, and the growth and dispersion of bacteria.

To achieve the above objective, as is shown in FIG. 1, an air conditioning system 1 comprises:

sterilization/deodorization gas supply means 10, which includes a chemical container 12 and an evaporation acceleration unit 14, for accelerating the performance of an evaporation process for the chemical container 12, and which is located along one part of an air channel. The chemical used for the present invention may be formalin or cresol, for example, and stabilized chlorine dioxide, which possesses especially superior sterilization and deodorization properties and is safe to handle, is especially used.

The chemical retained in the chemical container 12 can be a stabilized chlorine dioxide liquid, but preferably is a stabilized chlorine dioxide gel. And while the evaporation acceleration unit 14 can be constituted by ultraviolet irradiation means or heating means, it should be noted that the stabilized chlorine dioxide gas can be evaporated even at normal temperature when the heating means is provided as the evaporation acceleration unit. The stabilized chlorine dioxide solution may be retained in a cartridge container, which can be exchanged when the contents have been exhausted. It is preferable that the sterilization/deodorization gas supply means 10 constituted by these components be located along an air channel in the air conditioning system connecting an air inlet 20 and a heat exchanger (a cooled or heated air generator) 22.

The air conditioning system 1 may be a wall mounted or a suspended or embedded ceiling mounted room air conditioner, a package office air conditioner, a central air conditioner, or another type of air conditioner. The air conditioning system 1 may also be an air purifier or an air humidifier.

According to an air conditioning system that uses the sterilization/deodorization gas supply means of the invention, by utilizing the evaporation acceleration function of the evaporation acceleration unit 14, an appropriate amount of chlorine dioxide gas is generated from the stabilized chlorine dioxide solution retained in the chemical container 12, and the thus generated chlorine dioxide gas is mixed with air which is thereafter cooled or heated by thermal exchange while passing through various types of cooling or heating sources. The air/gas mixture thereafter passes through the interior of the air conditioner and into an air duct, and then, at an outlet, is discharged into a room to adjust the internal air temperature.

Since the sterilization/deodorization gas supply means 10 is located along the air channel between the air inlet 20 and the heat exchanger 22, the temperature of the air stream that contacts the stabilized chlorine dioxide solution in the chemical container 12 is the indoor air temperature, and since there is no great temperature difference, unlike when the air has been cooled or heated, the evaporation process is not adversely affected. While the room temperature will naturally differ in summer and in winter, such a difference can be coped with by adjusting the evaporation acceleration unit 14.

Heating using a heating source (heater) or ultraviolet irradiation using an ultraviolet lamp constitutes effective generation means for the evaporation acceleration unit 14. The ultraviolet lamp can be a fluorescent chemical lamp, wherein a structure for generating a great number of ultraviolet elements is employed for a mercury vapor-filled discharge tube having the same structure as a fluorescent lamp used for illumination.

Furthermore, according to the present invention, by properly adjusting the heating condition produced by a heating source, or the radiation of ultraviolet light by an ultraviolet lamp, the volume of the evaporated gas can be controlled. The radiation of the ultraviolet light can be adjusted by controlling the light radiated by the ultraviolet lamp or by positioning a filter or a partial shutter along the light path.

With this arrangement, sterilization/deodorization gas can be easily and securely mixed with air drawn into an air conditioning system. And as a result, the interior of the air conditioning system and air ducts can be sterilized and deodorized, and cooled or heated air mixed with the sterilization/deodorization gas can be supplied to an indoor area. Therefore, a clean and safe indoor air condition can be maintained by turning on or off the air conditioning system using a panel switch thereof or a remote control, or by using a timer.

BRIEF DESCRIPTION OF THE DRAWINGS

FIG. 1 is a diagram for explaining the basic structure of an air conditioning system that comprises sterilization/deodorization gas supply means according to the present invention.

DETAILED DESCRIPTION OF THE PREFERRED EMBODIMENT

Figure 2:
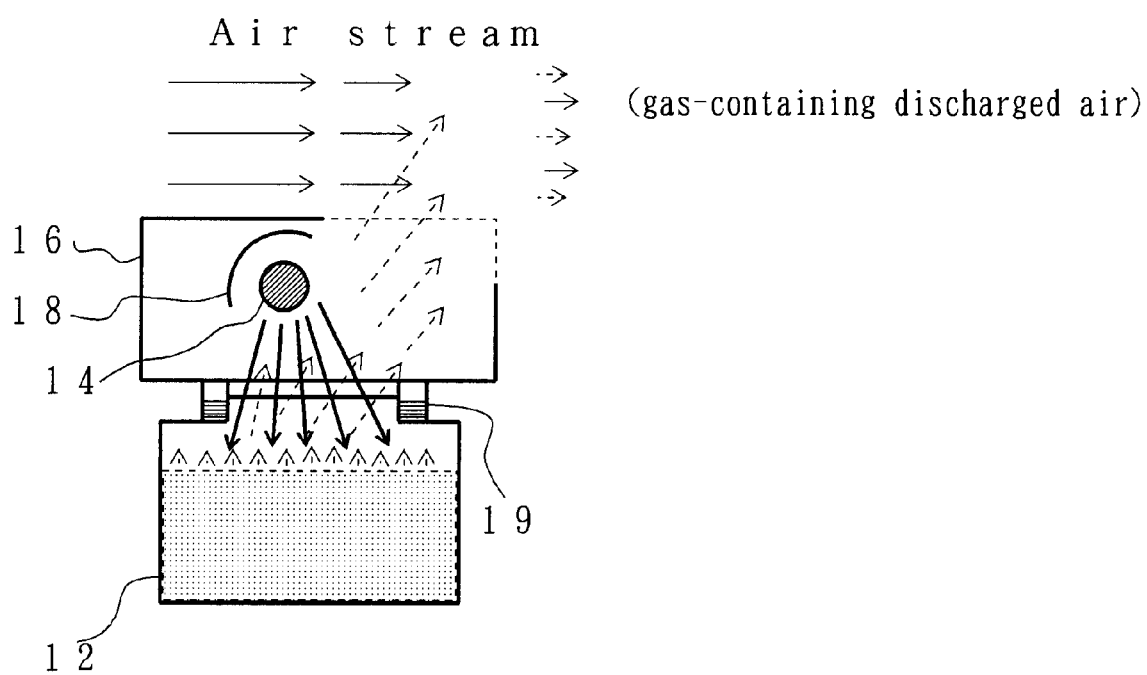
FIG. 2 is a diagram for explaining the basic structure of the sterilization/deodorization gas supply means.

An air conditioning system, in accordance with one embodiment of the present invention, comprising sterilization/deodorization gas supply means will now be described while referring to the accompanying drawings. In this embodiment, a stabilized chlorine dioxide gel is employed as a sterilization, deodorization and disinfection chemical for generating the sterilization/deodorization gas of the invention. The stabilized chlorine dioxide may be provided as an aqueous solution, or as a material that has been impregnated with the solution or that has absorbed the solution. The source for the generation of the sterilization/deodorization gas is not limited to stabilized chlorine dioxide, and can be another chemical, such as formalin or cresol, which can be used for sterilization and deodorization.

An explanation will now be given for the stabilized chlorine dioxide that is used as a primary element. A stabilized chlorine dioxide gel used in this invention can be manufactured by any well known means, such as a method according to which a bridging agent is mixed with agar or gelatin to form a gel. As for the chemical properties of chlorine dioxide, it is well known that it reacts strongly with a double linked portion and a benzene nucleus, and that it also reacts with a cyanide compound, hydrogen sulfide and protein, but that it rarely reacts with saturated and unsaturated fatty acids. By utilizing this property, a stabilized chlorine dioxide solution can be gelatinized by employing a gelatinized chemical obtained, for example, by mixing gelatin with a saturated fatty acid, such as stearic acid or palmitic acid, and an unsaturated fatty acid, e.g., sodium salt, such as oleic acid or linoleic acid.

The speed of evaporation attained by the stabilized chlorine dioxide gel can be adjusted in accordance with the amount of ethyl alcohol contained in the gelatinized chemical, and the size of the evaporation area in a container. The evaporation speed can also be varied by adjusting the strength of the ultraviolet radiation or the heating temperature, both of which greatly affect the vaporization speed. Also, since stabilized chlorine dioxide changes depending on the pH value, and is most stable at a reading of approximately pH 9, it is preferable that, as needed, an alkali material be added to the chlorine dioxide to maintain a pH 9 reading.

Since the stabilized chlorine dioxide gel is more suitable for storage, transportation and handling than is the aqueous solution, and can be safely employed using a small container, in this invention it is preferred that a cartridge container be filled with a stabilized chlorine dioxide gel, rather than with a stabilized chlorine dioxide aqueous solution.

FIG. 1 is a diagram showing the basic arrangement of the air conditioning system that comprises the sterilization/deodorization gas supply means of the invention. Sterilization/deodorization gas supply means 10 is constituted by a chemical container 12 and an evaporation acceleration unit 14, and is located along an air channel extending from an air inlet 20 in which a filter is mounted and a heat exchanger 22 that generates heated or cooled air.

A stabilized chlorine dioxide gel or liquid is retained in the chemical container 12. The evaporation acceleration unit 14 can be used as a heating source or as an ultraviolet ray radiation means, and is, for example, a fluorescent chemical lamp. Temperature adjustment means, an irradiation strength adjustment device and an operating timer (none of them shown) can be included, as needed, in the ultraviolet ray irradiation means. The heating source should be positioned for the best cooling effect, and is not necessary at normal temperatures.

When an ultraviolet lamp is employed as the evaporation acceleration unit 14, an appropriate ultraviolet radiation strength adjustment device can be an operating current control circuit for which a thyrister or another semiconductor device is used, or an ultraviolet transmission filter located along the irradiation path. In this case, it is appropriate for the operating current control circuit to exercise pulse control for a stable discharge having a predetermined or greater voltage pitch value, and for fluctuating an effective reflux. Further, a plurality of filters having different transmission levels are exchanged, in consonance with whether the operating mode of the air conditioning system is mainly for heating or for cooling and with whether the operating mode is set for summer or for winter, so that the air flow can be adjusted.

In this embodiment, in the air conditioning system 1 that is shown as a package air conditioner in FIG. 1, a compressor 24, which is schematically shown, compresses a heating medium to form a cooling source or a heating source that is combined with a heater, if possible, and the heat exchanger 22 cools or heats the air that passes through it. The air obtained following the thermal exchange is compressed by a fan 26, and is discharged through a grill 28 into a target space.

The sterilization/deodorization gas supply means 10 is located along the air channel which begins at the air inlet 20, wherein a filter is mounted. In the operation of the air conditioning system 1, when the sterilization/deodorization gas supply means 10 is activated, since air is introduced through the air inlet 20 before it reaches the heat exchanger 22, the evaporated, stabilized chlorine dioxide gas is mixed with the air to provide an appropriate relative density, and demonstrates sterilization/deodorization effects for the overall air channel in the air conditioning system 1. Therefore, the growth in the air conditioning system 1 of mold and other microorganisms, which generate bad odors, and bacteria can be efficiently suppressed.

The density of the chlorine dioxide gas in the air which is discharged into a target space, especially that which is discharged into a space wherein people are resident, should be restricted to around 0.33 ppm, a density which is harmless to humans. To control the density of the chlorine dioxide gas, either the manipulation of a switch on the panel of the air conditioning system or on a remote control, or a timer is employed to turn on or off the sterilization/deodorization gas supply means 10. As a result, a target indoor atmosphere can be maintained which is clean and safe for humans.

Since the stabilized chlorine dioxide gel or liquid retained in the chemical container 12 evaporates and the quantity is reduced as time elapses, the chemical must be appropriately supplemented as it is consumed. Therefore, it is preferable that the chemical container 12, including the evaporation acceleration unit 14, be constituted as a detachable cartridge relative to the sterilization/deodorization gas supply means 10. No particular limitations are placed on the size and the shape of the container 12, but while taking into account the fact that the size of the area contacted by the distributed air affects the efficiency of evaporation, a container 12 that is wider at the top will be convenient.

While in FIG. 1 the air conditioning system 1 for the embodiment is a package air conditioner, the air conditioning system may be constituted by a wall or ceiling suspended air conditioner, a wall or ceiling embedded air conditioner, or a central air conditioner. Furthermore, the air conditioning system 1 may be an air purifier or an air humidifier.

FIG. 2 is a diagram showing an example structure for the sterilization/deodorization gas supply means 10 wherein an ultraviolet lamp is employed as the evaporation acceleration unit 14. Stabilized chlorine dioxide gel is retained in the chemical container 12, and the ultraviolet lamp 14, which is integrally formed with a reflector cover 18 in the lamp chamber 16, efficiently irradiates with ultraviolet light the stabilized chlorine dioxide gel which is located below. It is preferable that the chemical container 12 be a cartridge that can be detachably coupled with the lamp chamber 16 using a connector 19.

With this arrangement, at least one part of the lamp chamber 16 is opened, and evaporated stabilized chlorine dioxide gas is discharged, as is indicated by broken-line arrows. Therefore, at an appropriate ratio, the chlorine dioxide gas is mixed with air flowing above, as indicated by solid arrows. The structure shown here is merely conceptual, and the actual arrangement should be variously modified in accordance with the size and the structure of the air conditioning system 1 for which the sterilization/deodorization gas supply means 10 is to be provided, and the structure of the space in which the system 1 is mounted.

As is described above, according to the air conditioning system including the sterilization/deodorization gas supply means of the invention, the sterilization/deodorization gas is generated in the air conditioning system as a mist or as a gas that contains no water. The sterilization/deodorization gas is not only active in the interior of the air conditioning system 1, but is also mixed, even though only slightly, with the air that is discharged through the grill into the target space. Therefore, the emission of mold, and microorganisms that may generate bad and unpleasant odors, and of infectious bacteria and irritants, such as those that are associated with respiratory infections, allergies and asthma can be considerably suppressed, and a satisfactory atmosphere can be maintained in the target space.

Further, since stabilized chlorine dioxide gel is employed, the chemical container can be prepared as a cartridge which is convenient to handle, and which is easy to store, transport and exchange.

Various modes of carrying out the invention are contemplated as being within the scope of the following claims, which specifically point out and distinctly describe the subject matter regarded as the invention.

What is claimed is:

1. An air conditioning system comprising:
   sterilization/deodorization gas supply means, which includes a chemical container wherein a chemical retained in said chemical container is selected from the group consisting of a stabilized chlorine dioxide gel and a stabilized chlorine dioxide liquid; and
   an ultraviolet irradiation device for accelerating the performance of an evaporation process by means of dispersion and evaporation of said chemical to form a sterilization/deodorization gas,
      wherein the chemical container and the ultraviolet irradiation device are located along one part of an air channel and are detachably coupled.

2. The air conditioning system according to claim 1, wherein said chemical container is a cartridge container, which is exchangeable when said chemical has been exhausted.

3. The air conditioning system according to claim 2, wherein said sterilization/deodorization gas supply means is located along an air channel in said air conditioning system connecting an air inlet and a heat exchanger.

4. The air conditioning system according to claim 3, wherein the sterilization/deodorization gas supply means is selectively turned on and off by one of a panel switch of said air conditioning system, a remote control, a timer and a combination thereof.

5. The air conditioning system according to claim 2, wherein the sterilization/deodorization gas supply means is selectively turned on and off by one of a panel switch of said air conditioning system, a remote control, a timer and a combination thereof.

6. The air conditioning system according to claim 1, wherein said sterilization/deodorization gas supply means is located along an air channel in said air conditioning system connecting an air inlet and a heat exchanger.

7. The air conditioning system according to claim 6, wherein the sterilization/deodorization gas supply means is selectively turned on and off by one of a panel switch of said air conditioning system, a remote control, a timer and a combination thereof.

8. The air conditioning system according to claim 1, wherein the sterilization/deodorization gas supply means is selectively turned on and off by one of a panel switch of said air conditioning system, a remote control, a timer and a combination thereof.

9. The air conditioning system according to any one of claims 1,2,6,3,8,5,7 or 4, wherein the air conditioning system is one of a wall mounted room air conditioner, a suspended room air conditioner, a ceiling mounted room air conditioner, a package office air conditioner, a central air conditioner, other air conditioner equipment and an air purifier.

* * * * *